United States Patent [19]

Cavazza

[11] Patent Number: 5,173,508

[45] Date of Patent: Dec. 22, 1992

[54] PHARMACEUTICAL COMPOSITIONS ACTIVE ON THE CARDIOVASCULAR SYSTEM, CONTAINING 3-METHYLTHIOPROPIONYL L-CARNITINE

[75] Inventor: Claudio Cavazza, Rome, Italy

[73] Assignee: Sigma-Tau Industrie Farmaceutiche Riunite S.p.A., Rome, Italy

[21] Appl. No.: 669,573

[22] Filed: Mar. 14, 1991

[30] Foreign Application Priority Data

Mar. 15, 1990 [IT] Italy .............................. 47759 A/90

[51] Int. Cl.$^5$ .......................................... A61K 31/225
[52] U.S. Cl. ........................................................ 514/547
[58] Field of Search .......................................... 514/547

[56] References Cited

U.S. PATENT DOCUMENTS

| | | | |
|---|---|---|---|
| 4,439,438 | 3/1984 | Cavazza | 424/263 |
| 4,590,209 | 5/1986 | Cavazza | 514/547 |
| 4,743,621 | 5/1988 | Cavazza | 514/547 |

OTHER PUBLICATIONS

Scislowski et al; CA 111(15):129142(n), Heart mitochondria metabolize 3-methylthiopropionate to carbon dioxide and methanethiol, 1989.
Scislowski et al. Biochem J 247(1) (1987), 35–40.

Primary Examiner—Marianne M. Cintins
Assistant Examiner—Rebecca Cook
Attorney, Agent, or Firm—Oblon, Spivak, McClelland, Maier & Neustadt

[57] ABSTRACT

3-methylthiopropionyl L-carnitine and its pharmacologically acceptable salts are active on the cardiovascular system, particularly in the treatment of myocardial anoxia, cardiac ischaemia, arrhythmias and congestive heart failure.

5 Claims, No Drawings

PHARMACEUTICAL COMPOSITIONS ACTIVE ON THE CARDIOVASCULAR SYSTEM, CONTAINING 3-METHYLTHIOPROPIONYL L-CARNITINE

The present invention relates to the use of 3-methylthiopropionyl L-carnitine and the pharmacologically acceptable salts thereof for the therapeutic treatment of disorders of the cardiovascular system.

As inner salt, 3-methylthiopropionyl has formula (I)

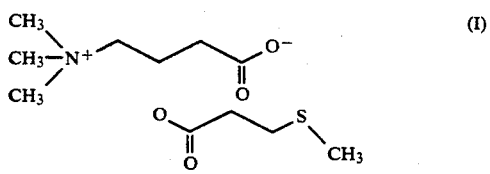

As compound salified with a pharmacologically acceptable acid, it has formula (I')

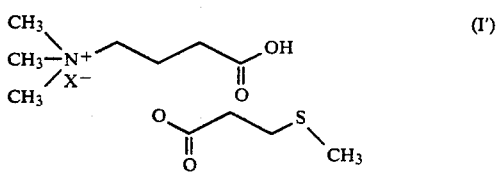

wherein $X^-$ is the anion of the pharmacologically acceptable acid. For instance, $X^-$ can be selected from chloride, bromide, orotate, acid aspartate, acid citrate, acid phosphate, acid fumarate, lactate, acid maleate, acid oxalate, acid sulfate and glucosephosphate.

It has been recently shown by Piotr W. D. Scislowski et al [Methionine metabolism by rat muscle and other tissues, occurrence of a new carnitine intermediate, Biochem. J. 247, 35-40 (1987) that 3-methylthiopropionyl L-carnitine is a natural substance that is synthesized during metabolism of methionine according to the scheme:

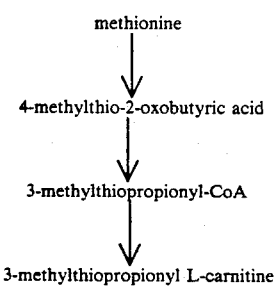

methionine
↓
4-methylthio-2-oxobutyric acid
↓
3-methylthiopropionyl-CoA
↓
3-methylthiopropionyl L-carnitine Moreover, these same Authors disclose the following synthesis route to the compound.

To date, 3-methylthiopropionyl L-carnitine has never been proposed as a drug. It has now been found that this compound, both as inner salt and as salt of a pharmacologically acceptable acid as previously described, is a potent drug for the therapeutic treatment of disorders of the cardiovascular system, particularly for the treatment of myocardial anoxia, cardiac ischaemia, arrhythmias and congestive heart failure.

Known compounds that are structurally related to 3-methylthiopropionyl L-carnitine, are disclosed in the Italian patent 1,170,862 (or in the corresponding U.S. Pat. No. 4,593,043). These compounds are mercaptoacylcarnitines, e.g. 3-mercaptopropionylcarnitine chloride. These compounds are known to be useful for the treatment of burnings and as mucolytic agents.

Other known compounds, even more vaguely related to 3-methylthiopropionyl L-carnitine from a structural viewpoint, that exhibit, however, the same therapeutic utility as that of the compound of the present invention, are certain alkanoylcarnitines, such as propionylcarnitine and butyrylcarnitine; cfr. Italian patent 1,155,813 (or the corresponding U.S. Pat. No. 4,194,006).

Unexpectedly, however, 3-methylthiopropionyl L-carnitine has been shown to be remarkably more potent than propionyl- and butyrylcarnitine in pharmacological tests suitable to assess its effect on the myocardial contractility, antiarrhythmic effect, antifatigue effect and other still.

The compounds of the present invention are orally or parenterally administered, in any of the usual pharmaceutical forms which are prepared by conventional procedures well-known to those persons skilled in the pharmaceutical technology. These forms include solid and liquid oral unit dosage forms such as tablets, capsules, solutions, syrups and the like as well injectable forms, such as sterile solutions for ampoules and phials.

For these pharmaceutical forms the usual solvents, diluents and excipients are used. Optionally, sweetening, flavouring and preservative agents can also be present. Non limiting examples of such agents are sodium carboxymethylcellulose, polysorbate, mannitol, sorbitol, starch, avicel, talcum and other agents which will be apparent to those skilled in the pharmaceutical technology.

The dose which is administered will be determined by the attending physician having regard to the age, weight and general conditions of the patient, utilizing sound professional judgement. Although effective results can be noticed at doses as low as 5 to 8 mg/kg of body weight daily, a dose of from about 10 to about 50 mg/kg of body weight is preferred. Whenever necessary, larger doses can be safely administered in view of the low toxicity of the compounds of this invention.

As non-limiting examples and depending on the specific pharmaceutical form of administration, the following dosages can be indicated:

for the phials: from 5 to 500 mg
for the capsules: from 15 to 50 mg
for the tablets: from 15 to 500 mg
for the oral solution: from about 15 to 50 mg

I claim:

1. A process for the treatment of myocardial anoxia, cardiac ischaemia, arrhythmias and congestive heart failure comprising administering to a patient in need of such treatment a pharmacologically effective amount of a pharmaceutical composition comprising a compound selected from the group consisting of the inner salt of 3-methylthiopropionyl L-carnitine (I)

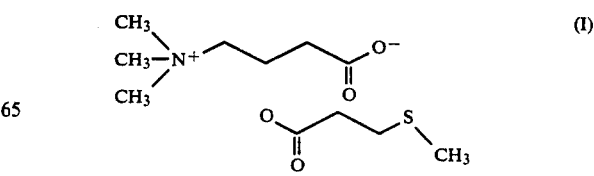

and salts of 3-methylthiopropionyl L-carnitine produced by salification with a pharmacologically acceptable acid (I')

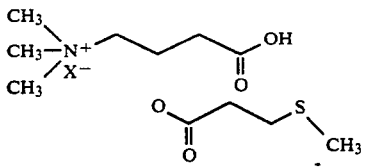
(I')

wherein X⁻ is the anion of said pharmacologically acceptable acid.

2. A process for the treatment of myocardial anoxia, cardia ischaemia, arrhythmias, and congestive heart failure, as claimed in claim 1, wherein X⁻ is an anion selected from the group consisting of fluoride, bromide, orotate, acid aspartate, acid citrate, acid phosphate, acid fumarate, lactate, acid maleate, acid oxalate, acid sulfate and glucosephosphate.

3. An orally or parenterally administrable pharmaceutical composition comprising a pharmacologically effective amount of a compound of Formula (I) or (I')

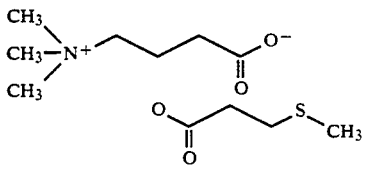
(I)

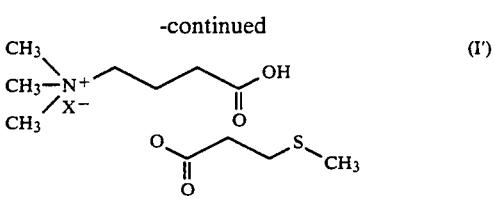
(I')

wherein X⁻ is an anion of a pharmacologically acceptable acid, as active principal and a pharmacologically acceptable carrier therefore.

4. An orally or parenterally administrable pharmaceutical composition for the therapeutic treatment of myocardial anoxia, cardiac ischaemia, arrhythmias and congestive heart failure, comprising a pharmacologically effective amount of a compound of Formula (I) or (I')

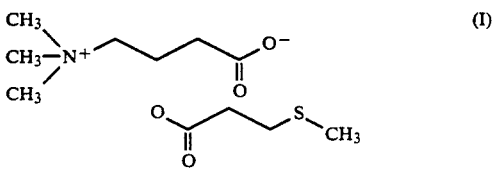
(I)

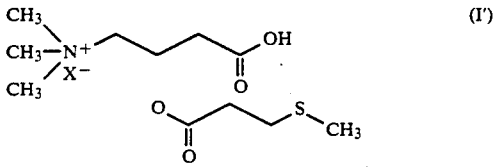
(I')

wherein X⁻ is an anion of a pharmacologically acceptable acid, as active principal and a pharmacologically acceptable excipient therefore.

5. A composition according to claim 4, in unit dosage form, comprising from about 5 to about 500 mg of said active principle.

* * * * *